United States Patent
Murata et al.

(10) Patent No.: US 10,648,961 B2
(45) Date of Patent: May 12, 2020

(54) CORE-SHELL TYPE CATALYST AND GAS SENSOR INCLUDING THE CATALYST

(71) Applicant: FUJI ELECTRIC CO., LTD., Kawasaki-shi, Kanagawa (JP)

(72) Inventors: Naoyoshi Murata, Hino (JP); Yukari Shibuta, Saitama (JP); Takuya Suzuki, Hachioji (JP); Makoto Okamura, Hachioji (JP)

(73) Assignee: FUJI ELECTRIC CO., LTD., Kawasaki-Shi, Kanagawa (JP)

( * ) Notice: Subject to any disclaimer, the term of this patent is extended or adjusted under 35 U.S.C. 154(b) by 191 days.

(21) Appl. No.: 15/455,113

(22) Filed: Mar. 9, 2017

(65) Prior Publication Data
US 2017/0269047 A1    Sep. 21, 2017

(30) Foreign Application Priority Data

Mar. 18, 2016   (JP) .................................. 2016-054603

(51) Int. Cl.
  *G01N 33/00*   (2006.01)
  *B01J 23/44*   (2006.01)
  *B01J 35/00*   (2006.01)
  *G01N 27/12*   (2006.01)
  *B01J 23/42*   (2006.01)

(52) U.S. Cl.
  CPC .......... *G01N 33/0047* (2013.01); *B01J 23/44* (2013.01); *B01J 35/008* (2013.01); *G01N 27/125* (2013.01); *G01N 33/0013* (2013.01); *G01N 33/0016* (2013.01); *B01J 23/42* (2013.01)

(58) Field of Classification Search
  CPC ............. G01N 33/0047; G01N 27/125; G01N 33/0013; G01N 33/0016; B01J 23/44; B01J 35/008
  See application file for complete search history.

(56) References Cited

U.S. PATENT DOCUMENTS

| | | | |
|---|---|---|---|
| 8,709,969 B2 * | 4/2014 | Lin .......................... | B01J 23/42 429/524 |
| 2001/0003916 A1 * | 6/2001 | Nomura ................. | G01N 27/12 73/31.06 |
| 2007/0281160 A1 * | 12/2007 | Krishna ................. | B01D 69/02 428/403 |

(Continued)

FOREIGN PATENT DOCUMENTS

| JP | 11-083781 | * | 3/1999 |
|---|---|---|---|
| JP | H1183781 A | | 3/1999 |

(Continued)

OTHER PUBLICATIONS

Gao, H. et al., "Journal of Power Sources ", NL, vol. 196, pp. 6138-6143.

*Primary Examiner* — Benjamin R Whatley
*Assistant Examiner* — Jacqueline Brazin
(74) *Attorney, Agent, or Firm* — Rabin & Berdo, P.C.

(57) ABSTRACT

A core-shell structure (a diameter is about 5 nm) is located on an $Al_2O_3$ catalyst support. Platinum (Pt metal) is a core, and a shell that surrounds the core has a solid solution structure $(A_{1-x}B_xO_y)$ (where X is a composition that composes A and B, and Y is a composition of oxygen (O)) that is composed of platinum, palladium, and oxygen.

17 Claims, 13 Drawing Sheets

(56) References Cited

U.S. PATENT DOCUMENTS

2010/0092841 A1* 4/2010 Lopez .................. B22F 1/0018
  429/409
2010/0272611 A1* 10/2010 Helwig ................. B82Y 15/00
  422/98
2017/0153214 A1* 6/2017 Wang ................. G01N 33/0062

FOREIGN PATENT DOCUMENTS

| JP | 3624928 B2 | 3/2005 |
| JP | 4010738 B2 | 11/2007 |
| JP | 2007-320847 A | 12/2007 |
| JP | 4958088 B2 | 6/2012 |

* cited by examiner

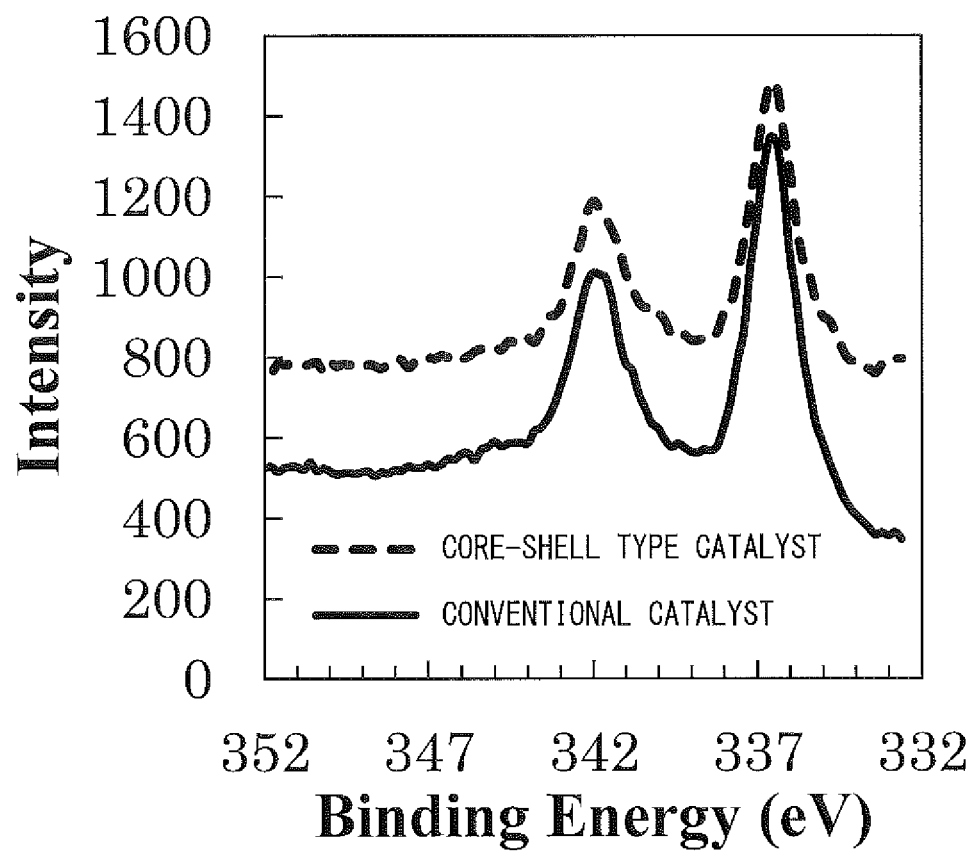
F I G. 4

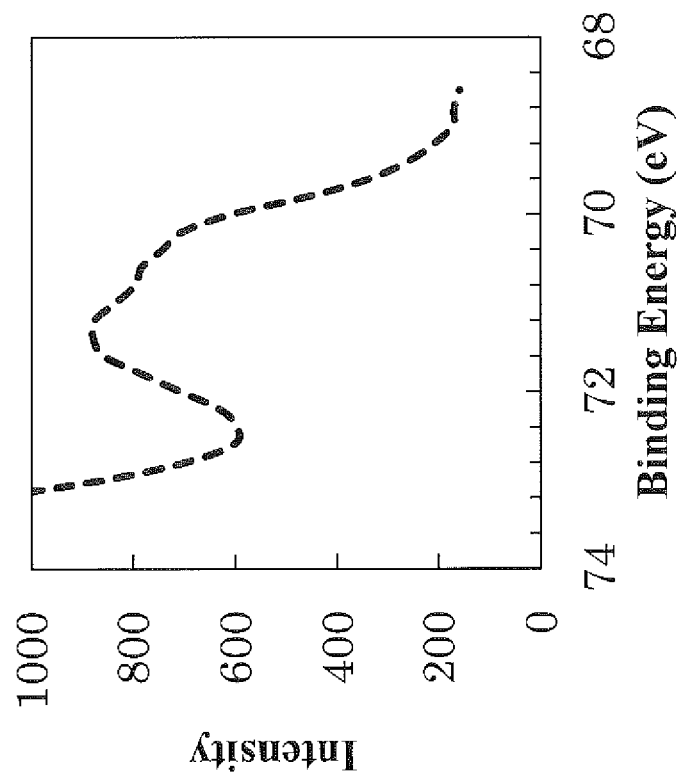
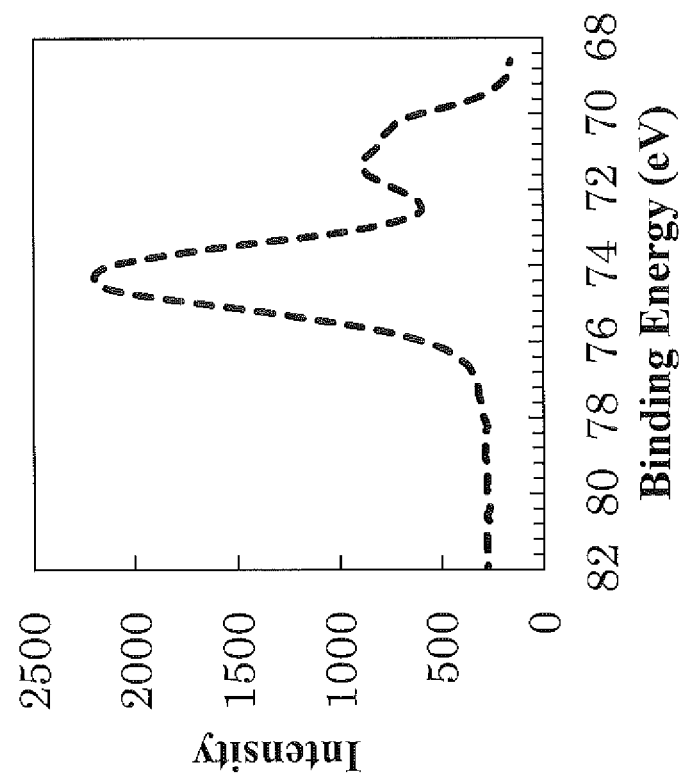
FIG. 5B
FIG. 5A

CORE-SHELL TYPE CATALYST AND GAS SENSOR INCLUDING THE CATALYST

CROSS-REFERENCE TO RELATED APPLICATIONS

This application is based upon and claims the benefit of priority of the prior Japanese Patent Application No. 2016-054603, filed on Mar. 18, 2016, the entire contents of which are incorporated herein by reference.

BACKGROUND OF THE INVENTION

Technical Field

The present invention relates to a core-shell type catalyst in which a core portion is composed of a single metal material and a shell portion is formed so as to have a solid-phase structure that is composed of two types of metal and oxygen, the core-shell type catalyst having a high oxidation activity, and a gas sensor including the catalyst. The phrase "solid-phase structure" means a structure in which an aggregate form of atoms is solid.

Background Art

Japanese Laid-Open Patent Publication No. 2007-320847 discloses a core-shell ceramic particulate and a method for manufacturing the core-shell ceramic particulate, but only a core-shell structure in which a shell portion is formed of a material comprised of one type of atom is provided.

In addition, Japanese Patent No. 3624928 discloses a method for manufacturing a platinum/palladium catalyst having a high oxidation activity. In Japanese Patent No. 3624928, a supporting method is specified to be manufacture by impregnation with a solution of platinum chloride and palladium chloride.

Further, Japanese Patent No. 4958088 discloses that heat treatment is performed on a core-shell type cerium oxide polymer hybrid particulate that is configured by a core portion formed of a cerium oxide particle and a shell portion formed of a layer of an organic polymer substance, and an obtained cerium oxide porous thick film is used as a gas sensor element (for example, a CO sensor).

SUMMARY OF THE INVENTION

A core-shell type catalyst according to an embodiment of the present invention includes a catalyst particulate including only atoms of a plurality of metal elements (such as for example more than one element from among the metal elements Pt, Pd, Ag, Au, Ni, Sn, Ir, Rh, Ru, Re, and Co) and atoms of a single non-metal element (such as oxygen), and a carrier (catalyst support) to immobilize the catalyst particulate. A core portion of the catalyst particulate is made up of only atoms of the single metal element, and a shell portion has a solid-phase structure that is composed of only atoms of the plurality of metal elements and the single non-metal element.

In the description above, two types of metal atoms are selected as the plurality of types of metal elements of the catalyst particulate from among Pt, Pd, Ag, Au, Ni, Sn, Ir, Rh, Ru, Re, and Co.

In the description above, the plurality of types of metal elements in the catalyst particulate are formed in such a way that an atomic ratio of the atoms included in any one of the metal elements of the plurality of metal elements to the atoms in another is 1:1.

In the description above, the solid-phase structure of the shell portion is expressed by the following general formula composed of two types of metal atoms and oxygen: $A_{1-x}B_xO_Y$ (where X is a composition that composes A and B, and Y is a composition of oxygen (O)).

In the description above, the best combination of general formulae expressing the solid-phase structure is A=Pd and B=Pt (X=0.5 and 0<Y≤1).

In any of the descriptions above, the catalyst support uses a material having a high specific surface, the material being mainly composed of any one type of metal oxide from among $Al_2O_3$, $Cr_2O_3$, $Fe_2O_3$, $Ni_2O_3$, $ZrO_2$, and $SiO_2$.

In any of the descriptions above, the solid-phase structure of the shell portion is a solid-phase structure of a plurality of types of metal atoms and a single type of non-metal atom.

A core-shell catalyst in any of the descriptions above is applied to an absorption layer of a gas detection unit that detects gas so as to generate a gas sensor.

The gas sensor described above includes: a gas detection unit that includes an absorption layer that absorbs gas (target gas) to be detected, a gas sensing layer that senses the gas to be detected, and a heater layer that heats the gas sensing layer; and a heater layer drive unit that drives the heater layer. The gas sensor heats the heater layer to 80° C. to 250° C., and detects whether gas exists.

The gas sensor described above includes: a gas detection unit that includes an absorption layer that absorbs gas to be detected, a gas sensing layer that senses the gas to be detected, and a heater layer that heats the gas sensing layer; and a heater layer drive unit that drives the heater layer. The gas sensor heats the heater layer to 300° C. to 400° C., and detects whether gas exits.

The gas sensor described above includes: a gas detection unit that includes an absorption layer that absorbs gas to be detected, a gas sensing layer that senses the gas to be detected, and a heater layer that heats the gas sensing layer; and a heater layer drive unit that drives the heater layer. The gas sensor heats the heater layer to 350° C. to 450° C., and detects whether gas exits.

The gas sensor described above heats the heater layer to 80° C. to 250° C. by intermittently driving the heater layer drive unit, and detects CO gas by detecting a gas detection signal that is sensed by the gas sensing layer via the gas absorption layer.

The gas sensor described above heats the heater layer to 300° C. to 400° C. by intermittently driving the heater layer drive unit, and detects LP gas (liquefied petroleum gas (LPG) by detecting a gas detection signal that is sensed by the gas sensing layer via the gas absorption layer.

The gas sensor described above heats the heater layer to 350° C. to 450° C. by intermittently driving the heater layer drive unit, and detects methane gas by detecting a gas detection signal that is sensed by the gas sensing layer via the gas absorption layer.

In the gas sensor in any of the descriptions above, the gas detection signal is a rate of change from an initial resistance value, the rate of change being sensed by the gas sensing layer.

BRIEF DESCRIPTION OF DRAWINGS

FIG. 4 is a graph illustrating states of Pd 3d XPS spectrums of the core-shell type catalyst according to the embodiment of the present invention and a conventional catalyst;

FIG. 5A is a graph illustrating a state of a Pt 4f XPS spectrum of the core-shell type catalyst according to the embodiment of the present invention;

FIG. 5B is a graph in which a portion of the Pt 4f XPS spectrum of the core-shell type catalyst according to the embodiment of the present invention is peak-enlarged;

DESCRIPTION OF EMBODIMENTS

Figure 1B:
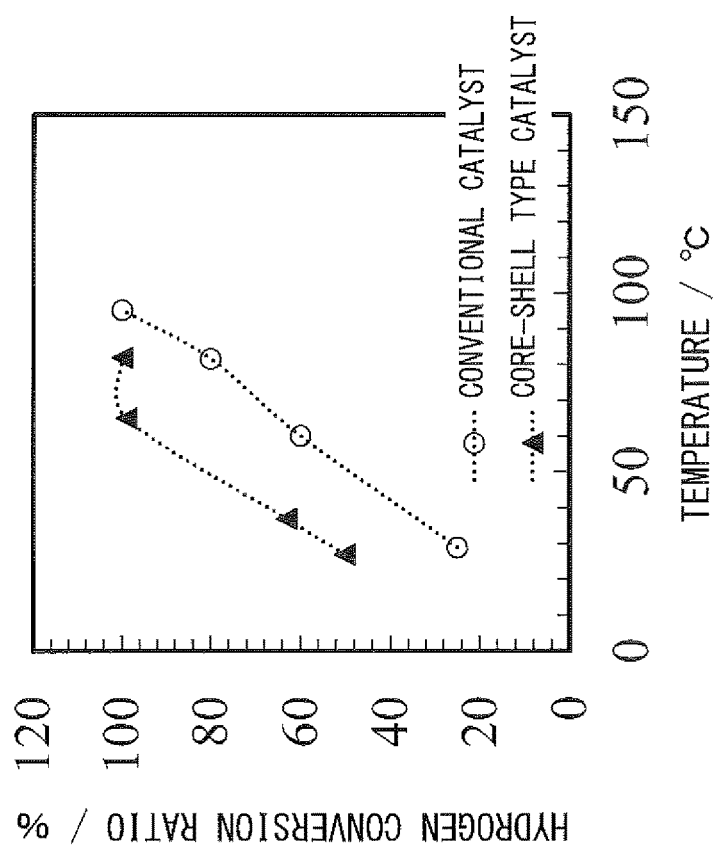
FIG. 1B is a graph illustrating a state of a hydrogen gas conversion ratio of the core-shell type catalyst according to the embodiment of the present invention.

An embodiment of the present invention is described below in detail.

Details of a core-shell type catalyst according to the embodiment of the present invention are itemized below.

(1) A core-shell type catalyst (a catalyst for a gas sensor) that supports platinum Pt metal and palladium Pd metal on a carrier (catalyst support) (for example, $Al_2O_3$) that is mainly composed of metal oxide to immobilize a catalyst particulate is manufactured by performing the following processes.

A catalyst support that is mainly composed of $Al_2O_3$, as described above, is best, and a catalyst support that is mainly composed of $ZrO_2$ is second best. Another catalyst support that is mainly composed of metal oxide that has a large surface area per unit volume, similarly to $Al_2O_3$ and $ZrO_2$, namely, metal oxide that has a high specific surface area, such as $Cr_2O_3$, $Fe_2O_3$, $Ni_2O_3$, or $SiO_2$, may be used.

First, a catalyst support (for example, $Al_2O_3$) is mixed with an amine aqueous solution (a nitride aqueous solution) including platinum Pt metal and palladium Pd metal, and the catalyst support is dried. Then, a first heat treatment (described later) is performed in an atmosphere including oxygen in a powdered state.

The best metal in the catalyst particulate above is a combination of Pt and Pd, as described above, but according to the present invention, any two types of bivalent metal element consisting of one type of atom may be selected from among Ag, Au, Ni, Sn, Ir, Rh, Ru, Re, and Co. If two types of bivalent metal element are included, an atomic ratio of two type of metal atoms in the catalyst particulate is preferably 1:1.

Platinum Pt and palladium oxide PdO are supported on the catalyst support (for example, $Al_2O_3$) by performing pyrolysis.

Then, a hydrogen reduction treatment that is a second heat treatment (described later) is performed in a nitrogen atmosphere including water vapor and hydrogen.

Further, an oxidation treatment that is a third heat treatment (described later) is performed in an atmosphere including oxygen so as to generate a catalyst. It is assumed that the type of gas to be sensed is methane $CH_4$.

(2) In the first heat treatment above, powder obtained by drying, as described above, is transferred to a quartz boat, and heat treatment is performed in dried air (an atmosphere including 20-100% oxygen) at a temperature of 600° C. by using an electric furnace for three hours so as to thermally decompose a catalyst raw material. The temperature and processing time of the first heat treatment are not limited to the above, and a similar effect can be achieved at a temperature of 600-650° C. in a processing time of 3-5 hours.

(3) In the second heat treatment above, the catalyst powder is entered into the electric furnace, and heat treatment is performed for two hours in an atmosphere in which the temperature of mixed gas of 50% nitrogen gas and 50% hydrogen gas is increased to 400° C., the mixed gas including water vapor by bubbling pure water. An amount of hydrogen gas, temperature, and processing time of the second heat treatment are not limited to the above, and a similar effect can be achieved in nitrogen including 30-50% hydrogen gas at a temperature of 350-450° C. in a processing time of 2 or more hours.

The second heat treatment is a process needed to desorb an element that is harmful for a catalyst when mixing the catalyst with an amine aqueous solution (a nitride aqueous solution). In a case in which no harmful elements are included, the second heat treatment can be omitted.

(4) In the third heat treatment after the second heat treatment, firing treatment is performed in an atmosphere including oxygen gas (20-100%) at a temperature of 580° C. for five hours. The temperature of the firing treatment is not limited to the above, and a similar effect can be achieved at a temperature of 550-650° C.

Figure 1A:
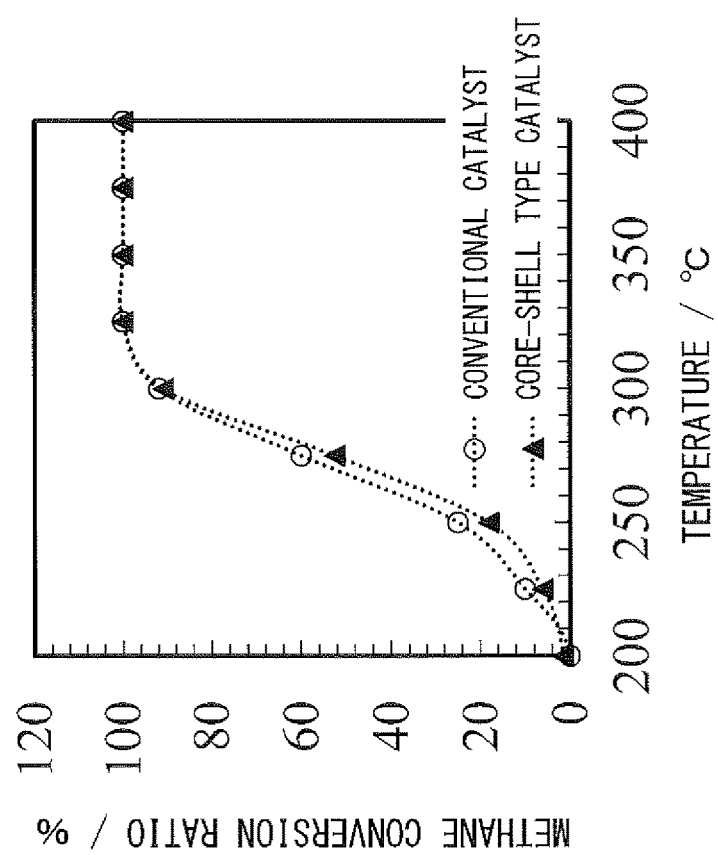
FIG. 1A is a graph illustrating a state of a methane gas conversion ratio of a core-shell type catalyst according to an embodiment of the present invention.

(5) FIG. 1A is a graph illustrating a state of a methane gas conversion ratio of a core-shell type catalyst according to the embodiment of the present invention. FIG. 1B is a graph illustrating a state of a hydrogen gas conversion ratio of the core-shell type catalyst according to the embodiment of the present invention.

The gas conversion ratio is measured by using a fixed-bed flow type catalyst evaluation device. Gas (target gas) to be detected ($CH_4$, $H_2$: 0.5%-Air) is flowed at a flow rate of 50 SCCM. A filler content is 0.143 cm³.

FIG. 1A illustrates a methane gas conversion ratio, and FIG. 1B illustrates a hydrogen gas conversion ratio. It is evident that the core-shell type catalyst according to this embodiment has a high activity to hydrogen in comparison with a conventional catalyst (for example, PdO) having a single-phase shell layer.

In order to examine a detailed structure of the core-shell type catalyst according to this embodiment that is manufactured as described above, high-angle annular dark-field scanning transmission electron microscopy (HAADF-STEM) analysis is performed.

In this HAADF-STEM observation technique, scattering of incident electrons and atoms is observed, and an atom having a larger atomic number is observed more brightly (whitely) on a display. It is well-known to those skilled in the art that platinum Pt has a larger atomic number than palladium Pd.

In addition, in order to examine a detailed structure of a shell portion, X-ray diffraction (XRD), X-ray photoelectron spectroscopy (XPS), and X-ray absorption near edge spectroscopy (XANES) are performed.

A peak intensity in an XANES spectrum is referred to as a white line height (WLH), and the magnitude of an intensity of platinum Pt corresponds to a valence.

Figure 2:
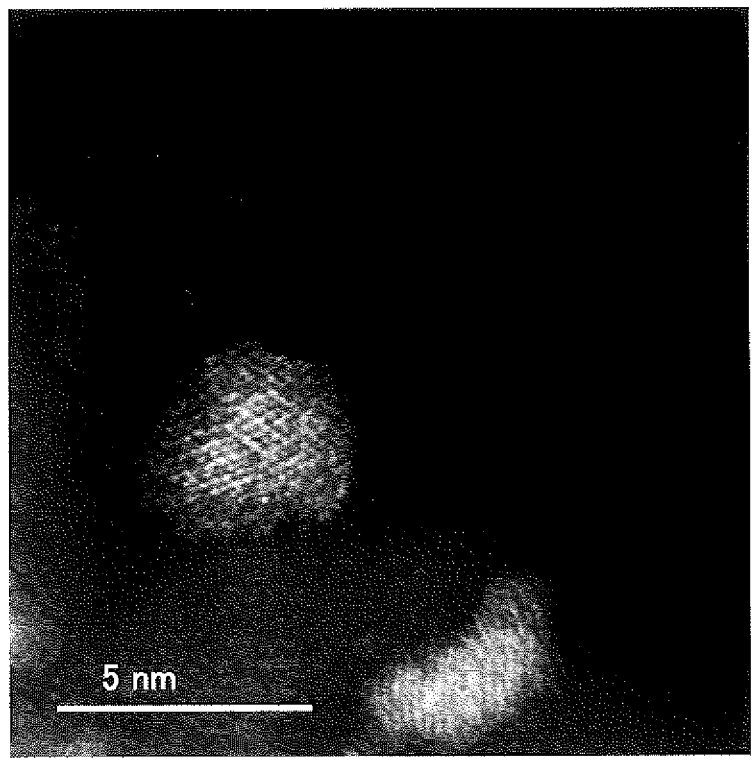
FIG. 2 illustrates an HAADF-STEM observation result of the core-shell type catalyst according to the embodiment of the present invention.

FIG. 2 illustrates an HAADF-STEM observation result of the core-shell type catalyst according to the embodiment of the present invention.

In FIG. 2, it is observed that a central portion of a catalyst particulate (a catalyst) shines white, and that a portion closer to an outer periphery includes a larger gray portion. In addition, white bright spots are slightly observed on the outer periphery of the catalyst particulate (the catalyst), and this shows that platinum Pt is included in an outer peripheral portion.

Further, the size of a catalyst can be grasped from a scale indicated in the HAADF-STEM observation result illustrated in FIG. 2.

This result shows that the core-shell type catalyst according to this embodiment that has a high oxidation activity has a core-shell structure, and that at least a core is composed of Pt metal (pure).

Figure 3:
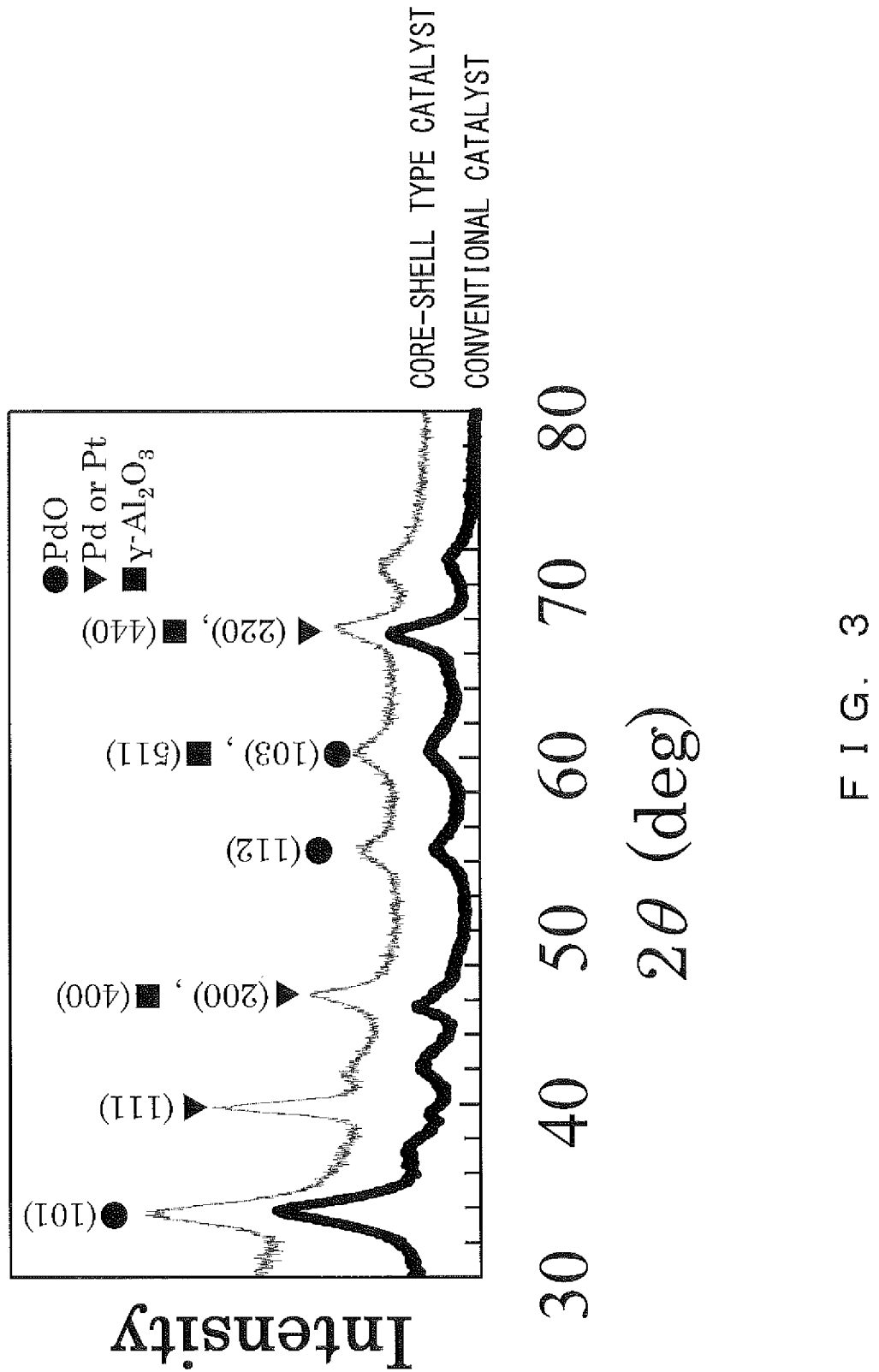
FIG. 3 is a graph illustrating an XRD analysis result of the core-shell type catalyst according to the embodiment of the present invention.

FIG. 3 is a graph illustrating an XRD analysis result of the core-shell type catalyst according to the embodiment of the present invention.

From the XRD (X-ray Diffraction) analysis result illustrated in FIG. 3, a pattern of metal derived from palladium Pd or platinum Pt and a tetragon derived from palladium oxide PdO is observed.

From the HAADF-STEM observation result illustrated in FIG. 2, it is estimated that a metal peak indicates platinum Pt of the core. On the other hand, it is estimated that a pattern of the tetragon derived from palladium oxide PdO reflects a shell structure.

TABLE 1

| catalyst | lattice parameter/Å | |
|---|---|---|
| | a = b | c |
| core-shell type catalyst | 3.077 | 5.279 |
| conventional catalyst | 3.032 | 5.355 |

Table 1 illustrates a lattice parameter of a tetragon that is calculated from the XRD pattern illustrated in FIG. 3. Table 1 shows a tendency that an a-axis lattice parameter increases and a c-axis lattice parameter decreases, in comparison with the conventional catalyst (for example, PdO) having a single-phase shell layer.

A result of calculating a lattice parameter in a model in which a platinum Pt atom is solutionized in palladium oxide PdO of the tetragon by performing a first principle calculation that is well-known to those skilled in the art also shows a similar tendency, and therefore it is understood that the shell structure of the core-shell type catalyst according to the embodiment of the present invention has a structure unique to $Pd_{1-x}Pt_xO$ in which palladium Pd sites in palladium oxide PdO are substituted with a platinum Pt atom.

When a solid-solution structure having the structure above unique to $Pd_{1-x}Pt_xO$ is further analyzed, the solid-solution structure above has a unique structure that is expressed by a general formula that is configured of two types of metal and oxygen, $A_{1-x}B_xO_Y$ (where X is a composition that composes A and B, and Y is a composition of O (oxygen)). It is preferable that the best combination of general formulae that expresses the solid-solution structure above be A=Pd, B=Pt (X=0.5, and 0<Y≤1).

FIG. 4 is a graph illustrating states of Pd 3d XPS spectrums of the core-shell type catalyst according to the embodiment of the present invention and a conventional catalyst.

From a Pd 3d XPS analysis result illustrated in FIG. 4, it is understood that a Pd chemical state of the core-shell type catalyst according to the embodiment of the present invention has the same divalent component as that of the convention catalyst having a single-phase shell layer.

FIG. 5A is a graph illustrating a state of a Pt 4f XPS spectrum of the core-shell type catalyst according to the embodiment of the present invention. FIG. 5B is a graph in which a portion of the Pt 4f XPS spectrum of the core-shell type catalyst according to the embodiment of the present invention is peak-enlarged.

A peak around 74 eV in the graph illustrated in FIG. 5A is a peak derived from $\gamma$-$Al_2O_3$, and a peak around 70-73 eV in the same graph is $4f_{7/2}$. FIG. 5B is an enlarged view of $4f_{7/2}$.

The Pt $4f_{7/2}$ peak illustrated in FIG. 5B shows that a peak exists on a high-energy side (around 71.8 eV) in addition to a peak of Pt metal around 71 eV. Therefore, it is understood that the core-shell type catalyst according to the embodiment of the present invention is in a state in which a valence is higher than Pt metal.

Figures 6A, 6B:
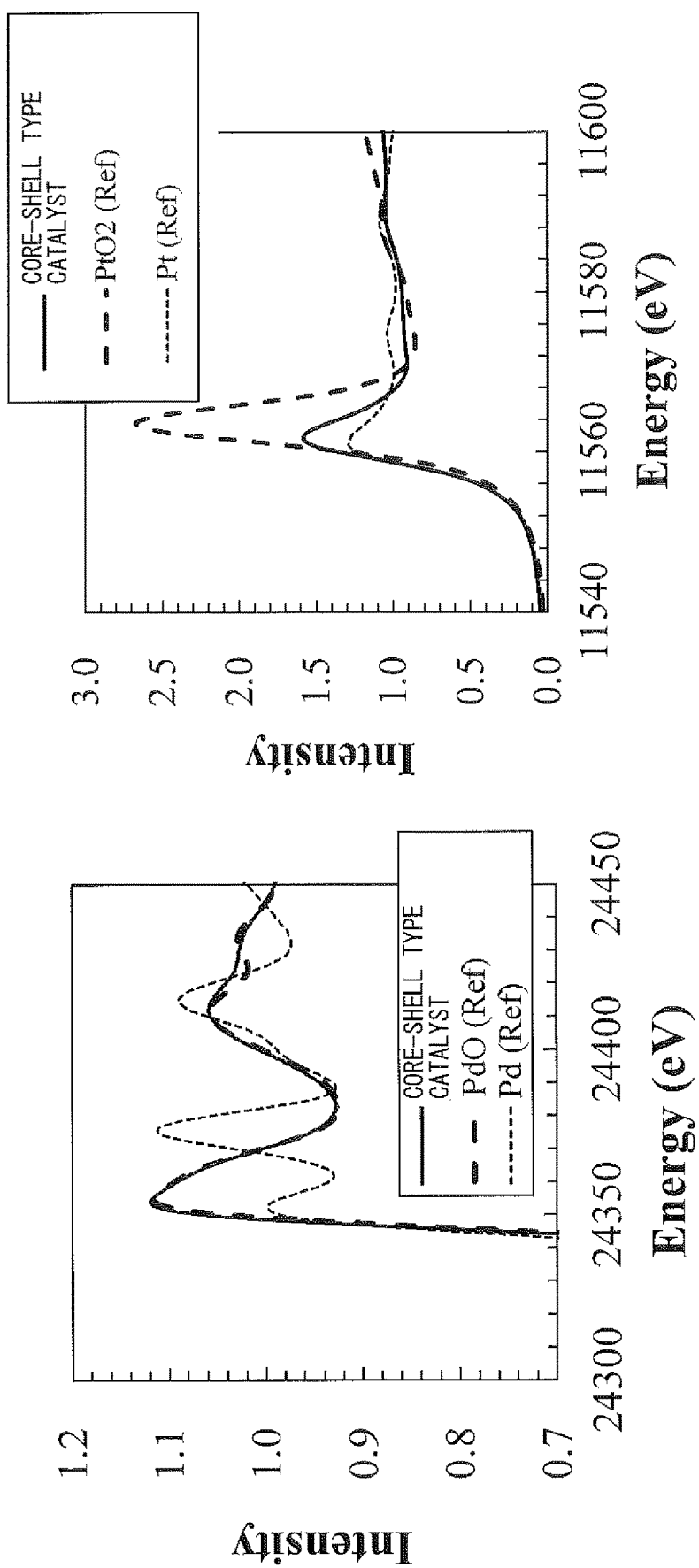
FIG. 6A is a graph illustrating a state of a Pd K-edge XANES spectrum of the core-shell type catalyst according to the embodiment of the present invention.
FIG. 6B is a graph illustrating a state of a Pt L-edge XANES spectrum of the core-shell type catalyst according to the embodiment of the present invention.

FIG. 6A is a graph illustrating a state of a Pd K-edge XANES spectrum of the core-shell type catalyst according to the embodiment of the present invention. FIG. 6B is a graph illustrating a state of a Pt L-edge XANES spectrum of the core-shell type catalyst according to the embodiment of the present invention.

In the Pd K-edge XANES spectrum illustrated in FIG. 6A, a spectrum of the core-shell type catalyst according to the embodiment of the present invention overlaps a spectrum of the conventional catalyst having a single-phase shell layer, and therefore it can be said that a Pd chemical state of the core-shell type catalyst according to the embodiment of the present invention includes the same divalent component as that of the conventional catalyst having a single-phase shell layer, as described above.

On the other hand, the Pt L-edge XANES spectrum illustrated in FIG. 6B shows that a WLH of the core-shell type catalyst according to the embodiment of the present invention is higher than Pt (metal), and is lower than $PtO_2$(Pt tetravalent). Therefore, it is estimated that a chemical state of platinum Pt is bivalent or trivalent. Matching this with the observation results above, it is highly likely that the chemical state of platinum Pt is bivalent.

Figure 7:
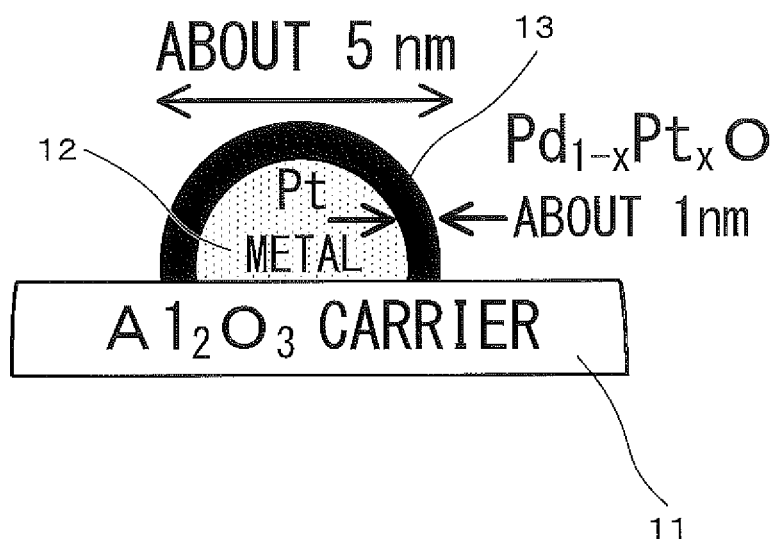
FIG. 7 is a schematic diagram illustrating the structure of the core-shell type catalyst according to the embodiment of the present invention.

FIG. 7 is a schematic diagram illustrating the structure of the core-shell type catalyst according to the embodiment of the present invention. Namely, FIG. 7 is a schematic diagram illustrating a catalyst structure obtained from the detailed structure analysis result above.

As is evident from FIG. 7, the core-shell type catalyst according to the embodiment of the present invention has a core-shell structure (a diameter is about 5 nm) on an $Al_2O_3$ support 11. Platinum (Pt metal) 12 is a core, and a shell 13 (a thickness is about 1 nm) that surrounds the core has a solid-solution structure that is composed of platinum, palladium, and oxygen.

The core-shell type catalyst having the solid-solution structure above has a high oxidation activity to hydrogen in comparison with the conventional catalyst having a single-phase shell layer, and the core-shell type catalyst is effective as an oxidation catalyst in addition to a catalyst for a gas sensor.

Figure 8:
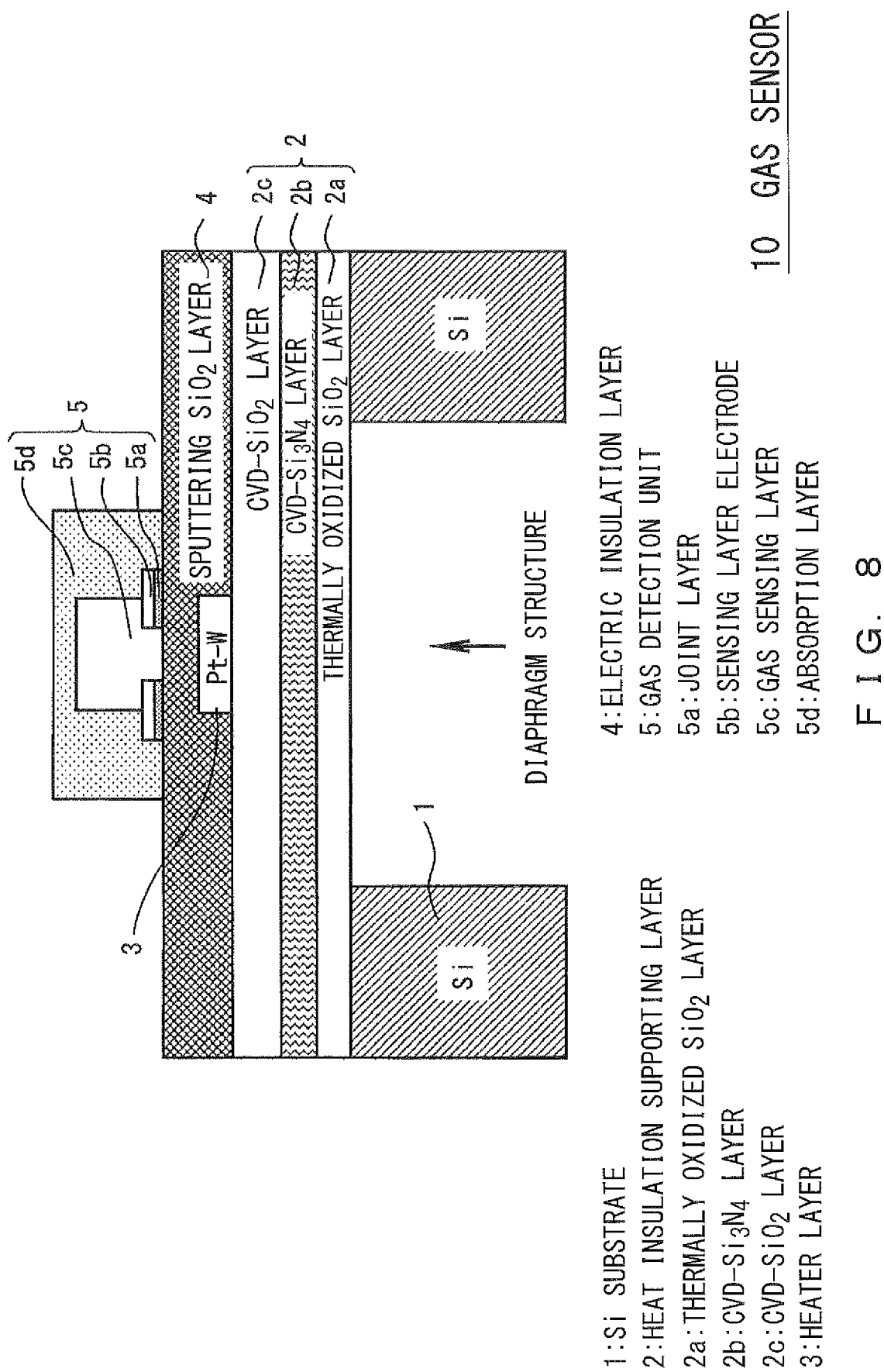
FIG. 8 illustrates an example of application of the core-shell type catalyst according to the embodiment of the present invention to a gas sensor having a diaphragm structure.

FIG. 8 illustrates an example of application of the core-shell type catalyst according to the embodiment of the present invention to a gas sensor having a diaphragm structure.

Specifically, the core-shell type catalyst is applied to an absorption layer 5d of a gas detection unit 5 in a gas sensor 10 illustrated in FIG. 8 having a diaphragm structure. A process for manufacturing a gas sensor has not been described above.

Accordingly, an outline of a process for manufacturing the gas sensor of FIG. 8 is described below.

The gas sensor 10 illustrated in FIG. 8 is a thin-film type semiconductor gas sensor, and the gas sensor 10 includes a silicon substrate (hereinafter referred to as an Si substrate) 1, a heat insulation supporting layer 2, a heater layer 3, an electric insulation layer 4, and a gas detection unit 5.

Figure 9:
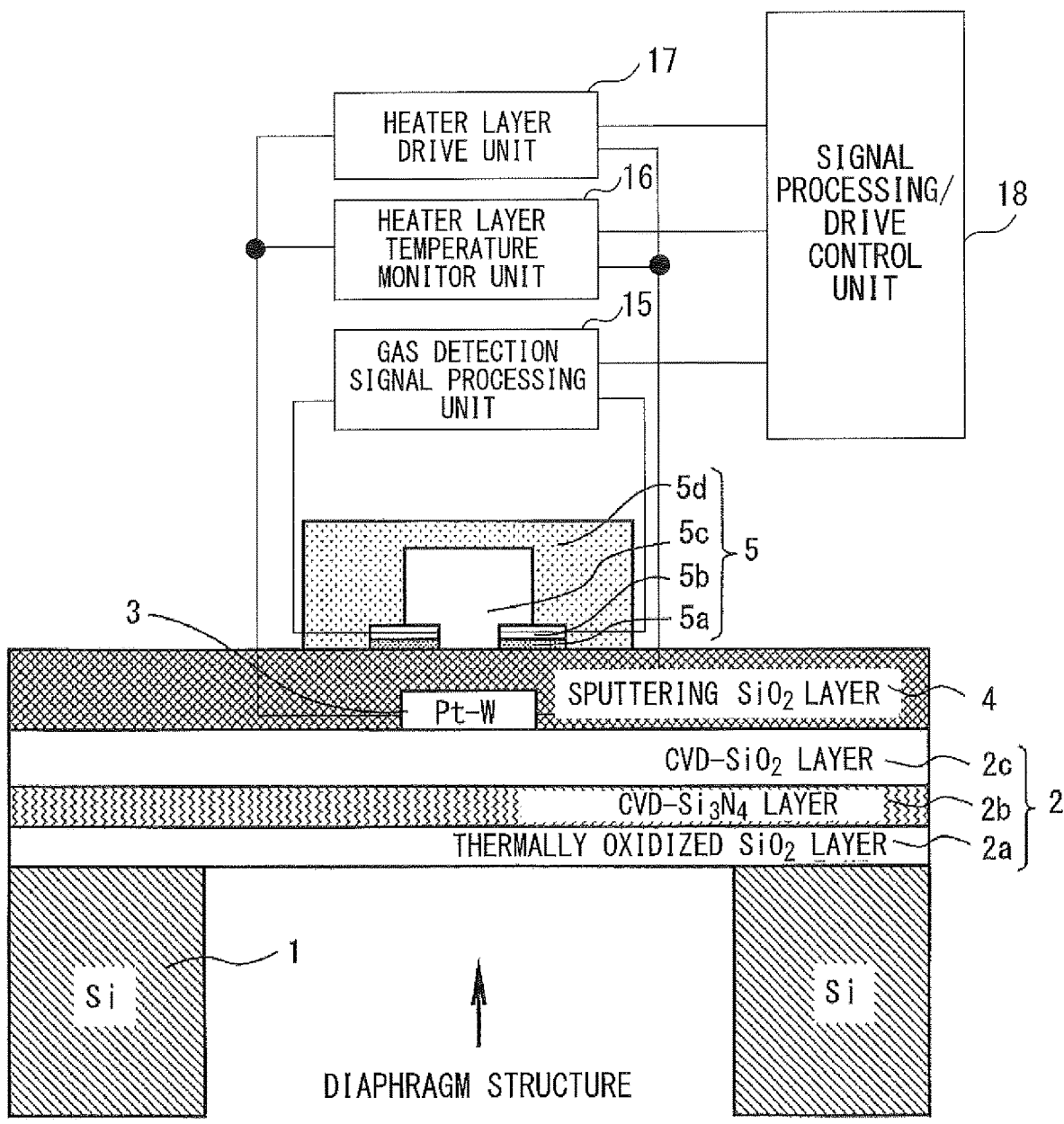
FIG. 9 illustrates an outline of driving and signal processing of a gas sensor according to the embodiment of the present invention.

The configurations of respective components illustrated in FIG. 8 are described while sometimes referring to FIG. 9.

The Si substrate 1 is formed of silicon (Si), and a through-hole is formed in a portion that is located just below the gas detection unit 5.

The heat insulation supporting layer 2 covers an opening of the through-hole so as to form a diaphragm, and the heat insulation supporting layer 2 is provided on the Si substrate 1.

Specifically, in the heat insulation supporting layer 2, a three-layer structure that includes a thermally oxidized $SiO_2$ layer 2a, a CVD-$Si_3N_4$ layer 2b, and a CVD-$SiO_2$ layer 2c is formed above the Si substrate 1, and the heat insulation supporting layer 2 has a diaphragm structure.

The thermally oxidized $SiO_2$ layer 2a is formed as a heat insulation layer, and the thermally oxidized $SiO_2$ layer 2a has a function of preventing heat generated in the heater layer 3 from being conducted to a side of the Si substrate 1 so as to reduce heat capacity. In addition, the thermally oxidized $SiO_2$ layer 2a is highly resistant to plasma etching, and the thermally oxidized $SiO_2$ layer 2a facilitates the formation of a through-hole in the Si substrate 1 by plasma etching, as described later.

The CVD-$Si_3N_4$ layer 2b is formed above the thermally oxidized $SiO_2$ layer 2a.

The CVD-$SiO_2$ layer 2c improves adhesiveness with the heater layer 3, and secures electric insulation. A $SiO_2$ layer according to chemical vapor deposition (CVD) has a small internal stress.

The heater layer 3 is formed by a thin-film Pt—W film or a Ni—Cr film, and the heater layer 3 is provided on an upper surface approximately in the center of the heat insulation supporting layer 2. In addition, a power supply line is formed. The power supply line is connected to a heater layer drive unit 17, as illustrated in FIG. 9.

The heater layer drive unit 17 heater-drives the heater layer 3. In addition, the heater layer 3 is electrically connected to a heater layer temperature monitor unit 16, as illustrated in FIG. 9, and the heater layer temperature monitor unit 16 measures an electric resistance of the heater layer 3.

The electric insulation layer 4 is a sputtering $SiO_2$ layer (a layer formed by sputtering) that electrically secures insulation, and the electric insulation layer 4 is provided so as to cover the heat insulation supporting layer 2 and the heater layer 3. The electric insulation layer 4 secures electric insulation between the heater layer 3 and sensing layer electrodes 5b. The electric insulation layer 4 also improves adhesiveness with a gas sensing layer 5 described later.

The gas detection unit 5 is provided above the electric insulation layer 4, and the gas detection unit 5 includes a pair of joint layers 5a, a pair of sensing layer electrodes 5b, a gas sensing layer 5c, and a gas absorption layer 5d.

The joint layers 5a are, for example, tantalum films (Ta films) or titanium films (Ti films), and the joint layers 5a are provided above the electric insulation layer 4 so as to be laterally symmetric to each other. The joint layers 5a are interposed between the sensing layer electrodes 5b and the electric insulation layer 4 so as to enhance joining strength.

The sensing layer electrodes 5b are, for example, platinum films (Pt films) or gold films (Au films), and the sensing layer electrodes 5b are provided as sensing electrodes of the gas sensing layer 5c so as to be laterally symmetrical to each other.

The gas sensing layer 5c is a tin dioxide layer (hereinafter referred to as an $SnO_2$ layer) doped with antimony (Sb), and the gas sensing layer 5c is formed above the electric insulation layer 4 so as to extend over the pair of sensing layer electrodes 5b. The gas sensing layer 5c has been described to be an $SnO_2$ layer in this example, but the gas sensing layer 5c may be a thin-film layer that is mainly composed of metal oxide such as $In_2O_3$, $WO_3$, ZnO, or $TiO_2$ which is a metal oxide, instead of the $SnO_2$ layer.

The gas absorption layer 5d is provided to cover surfaces of the electric insulation layer 4, the pair of joint layers 5a, the pair of sensing layer electrodes 5b, and the gas sensing layer 5c. The gas absorption layer 5d includes the core-shell type catalyst above that is configured by a catalyst particulate including a plurality of types of metal atoms (for example, Pt and Pd) and a single type of non-metal atom (for example, oxygen), and a support (for example, $Al_2O_3$) to immobilize the catalyst particulate. The first to third heat treatments above are performed such that a core portion of the catalyst particulate is a single metal material (for example, Pt) and a shell portion has a solid-solution structure which is composed of a plurality of metal materials (for example, Pt and Pd) and a single non-metal material (for example, oxygen), and the gas absorption layer 5d is manufactured as a sintered compact on a catalyst support $Al_2O_3$. This will also be described later.

$Al_2O_3$ is porous, and therefore $Al_2O_3$ increases an opportunity for gas passing through a hold to come into contact with the core-shell type catalyst above. $Al_2O_3$ accelerates a combustion reaction of reducing gas (disturbance gas) having a higher oxidation activity than gas to be detected, and the selectivity of the gas to be detected is enhanced. Namely, the disturbance gas can be oxidized and removed from the gas to be detected.

A member to support the gas absorption layer $5d$ may be mainly composed of metal oxide such as $Cr_2O_3$, $Fe_2O_3$, $Ni_2O_3$, $ZrO_2$, $SiO_2$, or zeolite, instead of $Al_2O_3$ above.

The gas detection unit 5 above (specifically, the gas sensing layer $5c$ via the sensing layer electrodes $5b$) is electrically connected to a gas detection signal processing unit 15 illustrated in FIG. 9, and a signal processing/drive control unit 18 reads a sensor resistance value via the gas sensing layer $5c$. This will be described later.

Accordingly, the gas sensor 10 employs a diaphragm structure so as to have a structure with a high heat insulation and a low heat capacity.

In addition, respective components in the gas sensor 10, namely, the sensing layer electrodes $5b$, the gas sensing layer $5c$, the gas absorption layer $5d$, and the heater layer 3, can be made to have a small heat capacity by using a technology such as micro electro mechanical systems (MEMS).

Consequently, temperature rapidly changes to a gas detection temperature, and gas can be detected in a short drive time. This results in a low power consumption.

Now, a method for manufacturing the gas sensor illustrated in FIG. 8 is generally described, and an outline of driving and signal processing for a gas sensor according to the embodiment of the present invention is described with reference to FIG. 9.

First, thermal oxidation is performed on one side (or both sides) of a plate silicon wafer (not illustrated) by using a thermal oxidation method, and the thermally oxidized $SiO_2$ layer $2a$ that is a thermally oxidized $SiO_2$ film is formed.

A CVD-$Si_3N_4$ film that is a supporting film is deposited on an upper surface on which the thermally oxidized $SiO_2$ layer $2a$ is formed, by using a plasma CVD method, and the CVD-$Si_3N_4$ layer $2b$ is formed.

A CVD-$SiO_2$ film that is a heat insulation film is deposited on an upper surface of the CVD-$Si_3N_4$ layer $2b$, and the CVD-$SiO_2$ layer $2c$ is formed.

A Pt—W film (or a Ni—Cr film) is vapor-deposited on an upper surface of the CVD-$SiO_2$ layer $2c$ by sputtering, and the heater layer 3 is formed.

A sputtering $SiO_2$ film is vapor-deposited on upper surfaces of the CVD-$SiO_2$ layer $2c$ and the heater layer 3 by sputtering, and the electric insulation layer 4 that is a sputtering $SiO_2$ layer is formed.

The pair of joint layers $5a$ and the pair of sensing layer electrodes $5b$ are formed on the electric insulation layer 4. Film formation is performed by using an RF magnetron sputtering device according to a usual sputtering method.

A film formation condition is the same between the joint layers (Ta or Ti) $5a$ and the sensing layer electrodes (Pt or Au) $5b$, and the film formation condition is that the pressure of argon gas (Ar gas) is 1 Pa, the temperature of a substrate is 300° C., RF power is 2 W/cm$^2$, and the film thicknesses of the joint layer $5a$ and the sensing layer electrode $5b$ are 500 Å and 2000 Å, respectively. The pair of sensing layer electrodes $5b$ are electrodes to extract an electric signal from the gas sensing layer $5c$.

A tin dioxide film (an $SnO_2$ film) extends over the pair of sensing layer electrodes $5b$ and is vapor-deposited on the electric insulation layer 4 by sputtering, and the gas sensing layer $5c$ is formed.

This film formation is performed by reactive sputtering by using an RF magnetron sputtering device. $SnO_2$ including 0.1 wt % antimony (Sb) is used as a target.

A film formation condition is that the pressure of Ar+$O_2$ gas is 2 Pa, the temperature of a substrate is 150-300° C., RF power is 2 W/cm$^2$, and film thickness is 400 nm.

Then, the gas absorption layer $5d$ is formed. The gas absorption layer $5d$ is manufactured according to the method above for manufacturing a core-shell catalyst. This method has been described above, and its description is omitted.

The diameter of the gas absorption layer $5d$ is made to be larger than that of an outer peripheral portion of the gas sensing layer $5c$ such that the gas absorption layer $5d$ sufficiently covers the gas sensing layer $5c$. Alternatively, the gas absorption layer $5d$ may be formed so as to be deposited on an upper surface of the gas sensing layer $5c$ in a state in which the size of the gas absorption layer $5d$ is the same as that of the gas sensing layer $5c$.

Finally, microfabrication processing for removing silicon from a reverse surface of the silicon wafer (not illustrated) by etching is performed, and the Si substrate 1 having a through-hole is formed. Consequently, the gas sensor 10 having a diaphragm structure is finally formed.

As illustrated in FIG. 9, the heater layer 3 is electrically connected to the heater layer drive unit 17 and the heater layer temperature monitor unit 16, the sensing layer electrodes $5b$ are electrically connected to the gas detection signal processing unit 15, and the heater layer 3 and the sensing layer electrodes $5b$ are controlled by the signal processing/drive control unit 18.

The characteristic of the gas sensor manufactured above is described with reference to FIG. 10 through FIG. 13.

In FIG. 10 through FIG. 13, in a comparative example that is illustrated in order to explain the characteristic of the gas sensor, a gas sensor is used in which the gas absorption layer $5d$ above is manufactured by performing known screen printing using a paste that is formed of γ-alumina ($Al_2O_3$) with 7.0 wt % Pd added.

On the other hand, in the present example described above, a gas sensor is used in which the gas absorption layer $5d$ is manufactured by performing screen printing immediately above tin oxide ($SnO_2$) that is the gas sensing layer $5c$, using a paste that is formed of γ-alumina ($Al_2O_3$) with 7.0 wt % Pd and 14.0 wt % Pt added, and by performing firing.

The gas sensor manufactured as above is further described with reference to FIGS. 10 to 13.

Figure 10:
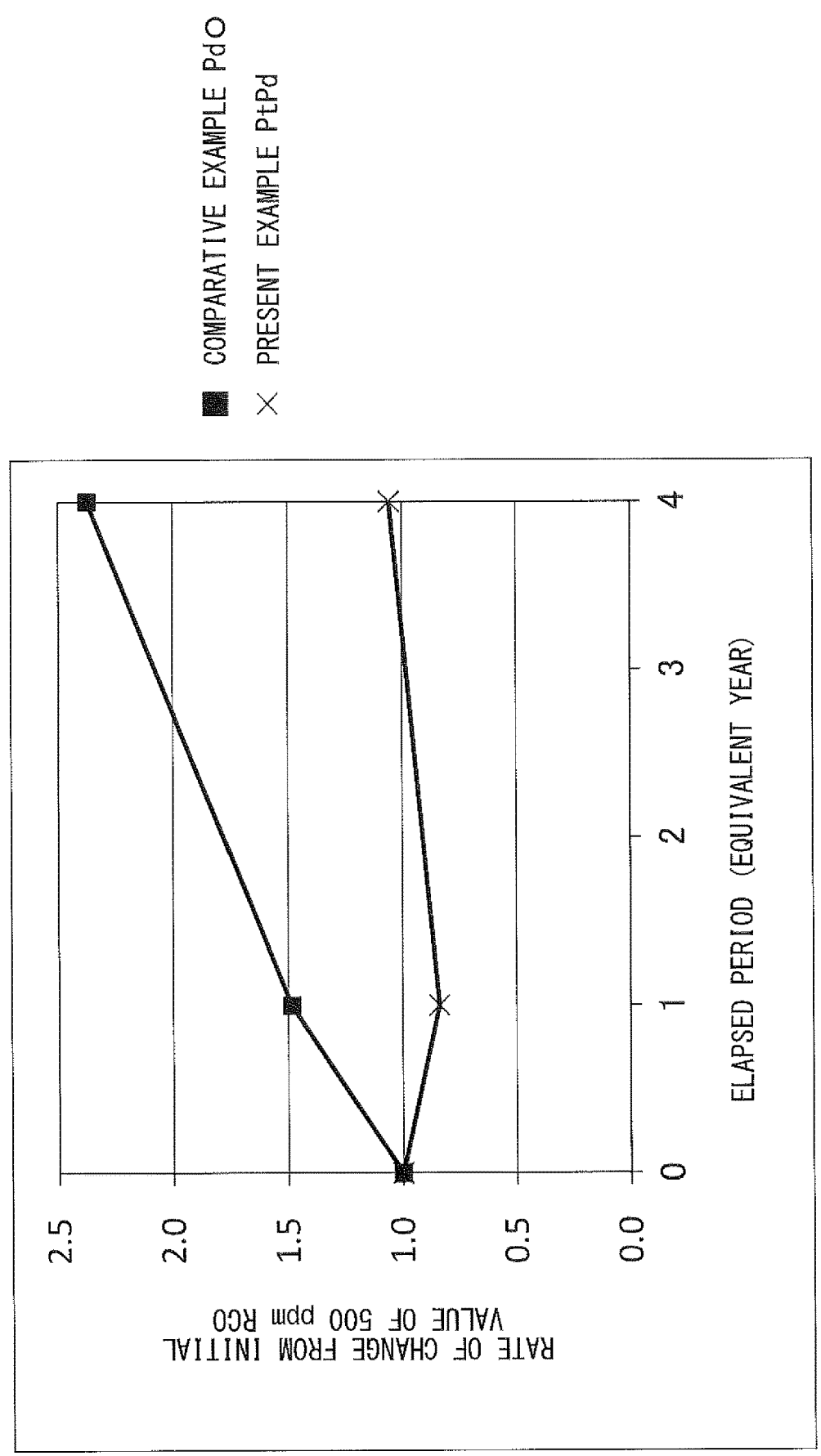
FIG. 10 is a characteristic diagram (no. 1) of a gas sensor manufactured according to the embodiment of the present invention.

FIG. 10 is a characteristic diagram (no. 1) of a gas sensor manufactured according to the embodiment of the present invention. FIG. 10 illustrates a result of examining whether the manufactured gas sensor conforms to the detection of carbon monoxide (CO) gas.

Namely, FIG. 10 illustrates rates of a change in a sensor resistance value with respect to 500 ppm CO at an equivalent driving year in an actual using environment in the example of the present invention and the comparative example.

In this case, the gas detection signal processing unit 15 illustrated in FIG. 9 is set to detect CO gas, and gas is detected at a heater temperature of 80° C. to 250° C.

The rate of a change in a sensor resistance value illustrated in FIG. 10 is a value obtained by dividing a sensor resistance value at each of the elapsed years by a sensor resistance value at elapsed day 0.

FIG. 10 illustrates that a rate of change from an initial resistance value in the example of the present invention is smaller than that in the comparative example in a test under a high-temperature high-humidity environment. In the example of the present invention, a sensor resistance value is stable even under the high-temperature and high-humidity environment, and therefore it is understood that the present example can be used to detect carbon monoxide (CO) gas.

Figure 11:
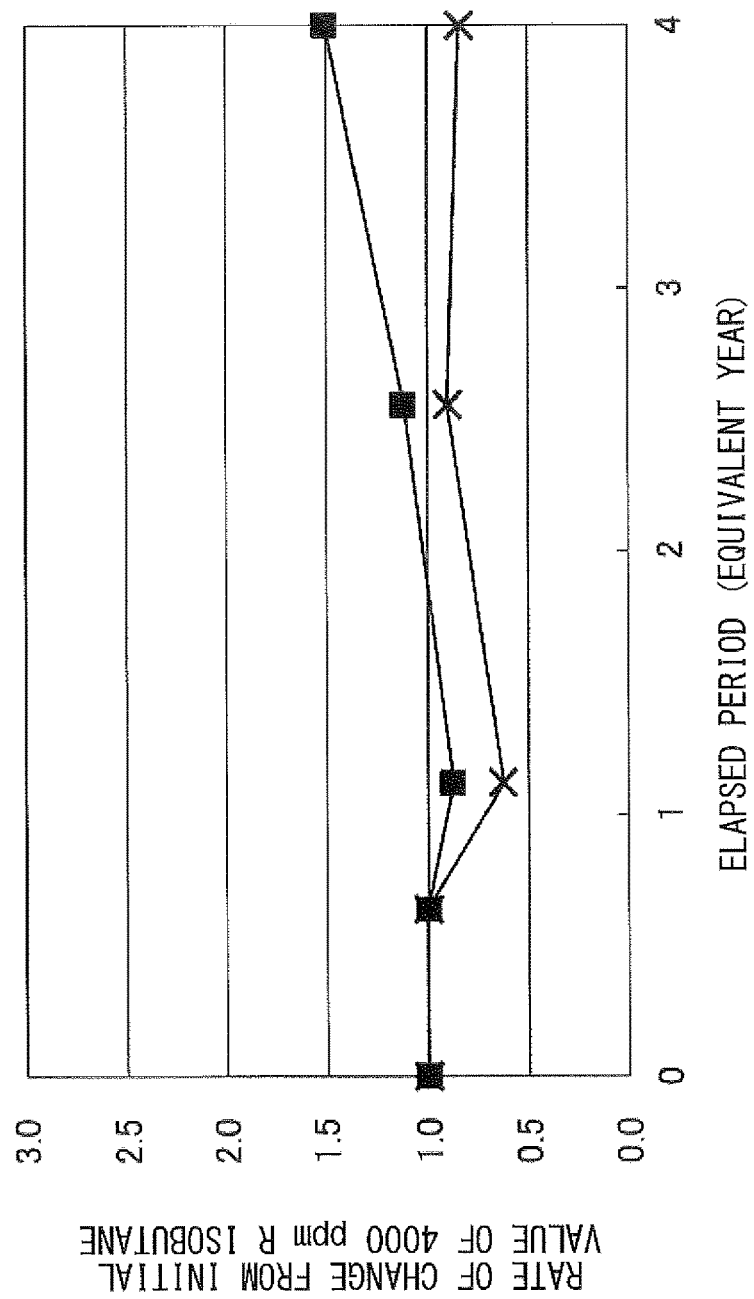
FIG. 11 is a characteristic diagram (no. 2) of a gas sensor manufactured according to the embodiment of the present invention.

FIG. 11 is a characteristic diagram (no. 2) of a gas sensor manufactured according to the embodiment of the present invention. FIG. 11 illustrates a result of examining whether the manufactured gas sensor conforms to the detection of isobutane.

Namely, FIG. 11 illustrates rates of a change in a sensor resistance value with respect to 400 ppm isobutane $C_4H_{10}$ at an equivalent driving year in an actual using environment in the example of the present invention and the comparative example.

In this case, the manufactured gas sensor is energized in a cycle of 22.5 seconds under the high-temperature and high-humidity environment, and a sensor resistance value with respect to isobutane $C_4H_{10}$ is measured. A heater temperature in this case is 300° C. to 400° C.

In addition, the gas detection signal processing unit 15 illustrated in FIG. 9 is set to detect isobutane $C_4H_{10}$.

In FIG. 11, it is assumed that a rate of a change in a sensor resistance value is a value obtained by dividing a sensor resistance value at each elapsed year by a sensor resistance value at elapsed day 0.

FIG. 11 illustrates that there is no large difference in a rate of change between the comparative example and the present example during a period to equivalent elapsed year 2.5. However, after the period, a rate of a change in a sensor resistance value increases in the comparative example, and it is observed that deterioration of a sensor proceeds. In the present example, the rate of change hardly changes even at equivalent elapsed year 4.

From the results above, it is considered that it has been confirmed that a gas sensor (a gas sensor for isobutane) having a higher humidity resistance is obtained by using a core-shell type catalyst having an atomic ratio of Pd and Pt of 1:1 as the gas absorption layer 5d of the gas sensor, in comparison with the case of a conventional PdO catalyst. LP gas includes isobutane $C_4H_{10}$, and therefore it is obvious that the gas sensor above can also be used as a sensor for LP gas.

Figure 12:
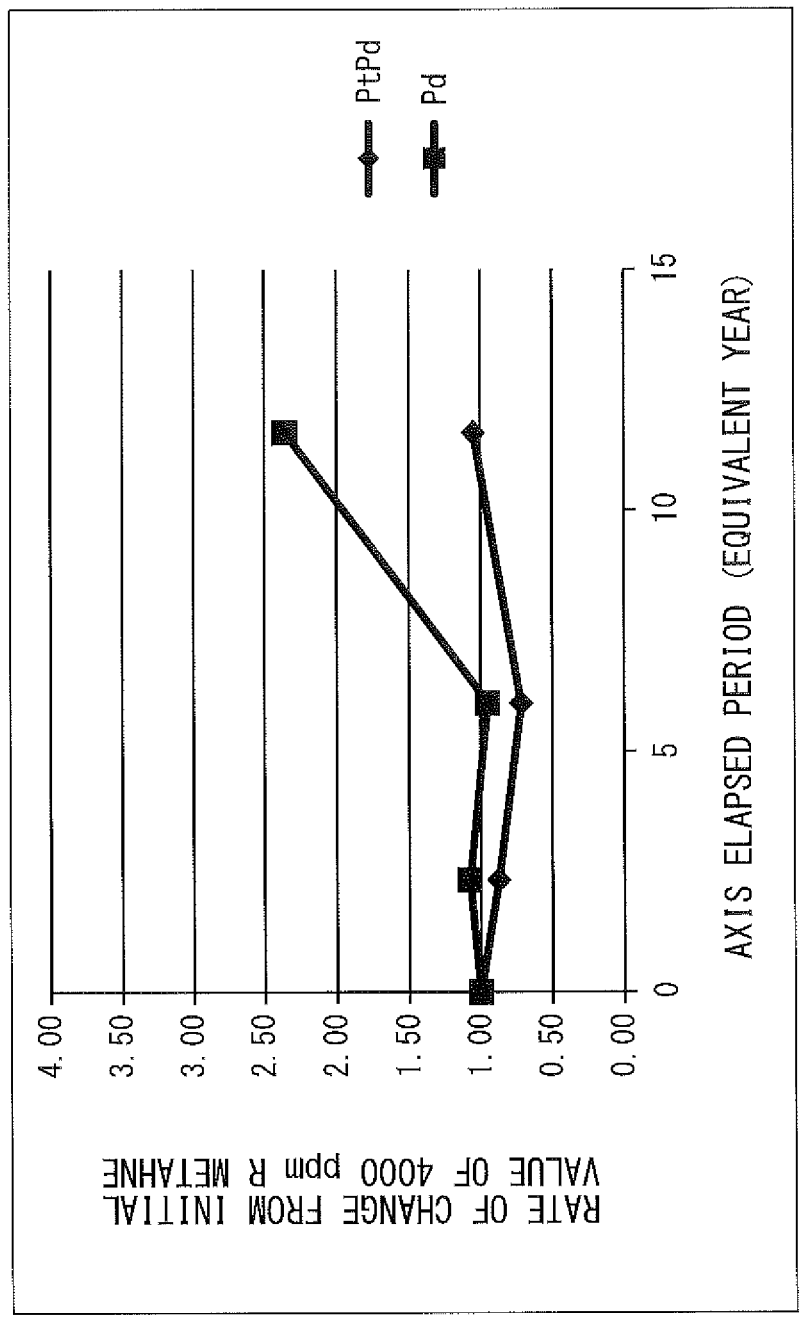
FIG. 12 is a characteristic diagram (no. 3) of a gas sensor manufactured according to the embodiment of the present invention.

FIG. 12 is a characteristic diagram (no. 3) of a gas sensor manufactured according to the embodiment of the present invention. FIG. 12 illustrates a result of examining whether the manufactured gas sensor conforms to the detection of methane.

Namely, FIG. 12 illustrates rates of a change in a sensor resistance value with respect to 4000 ppm methane at an equivalent driving year in an actual using environment in the example of the present invention and the comparative example.

In this case, settings in the gas detection signal processing unit 15 illustrated in FIG. 9 is changed from the settings above to detect carbon monoxide CO or isobutane $C_4H_{10}$ to settings to detect methane gas. Gas is detected at a heater temperature of 350° C. to 450° C.

It is assumed that a rate of a change in a sensor resistance value illustrated in FIG. 12 is a value obtained by dividing a sensor resistance value at each elapsed year by a sensor resistance value at elapsed day 0.

FIG. 12 illustrates that there is no large difference in a rate of change from an initial resistance value during a period to equivalent elapsed year 6 in a test under the high-temperature and high-humidity environment, between the example of the present invention and the comparative example.

However, at equivalent elapsed years that follow, a rate of change from an initial resistance value in the example of the present invention is smaller than that in the comparative example, similarly to the above rates of change in CO and isobutane. In the example of the present invention, a sensor resistance value is stable even under the high-temperature and high-humidity environment, and therefore it is understood that the present example can be used to detect methane gas.

Figure 13:
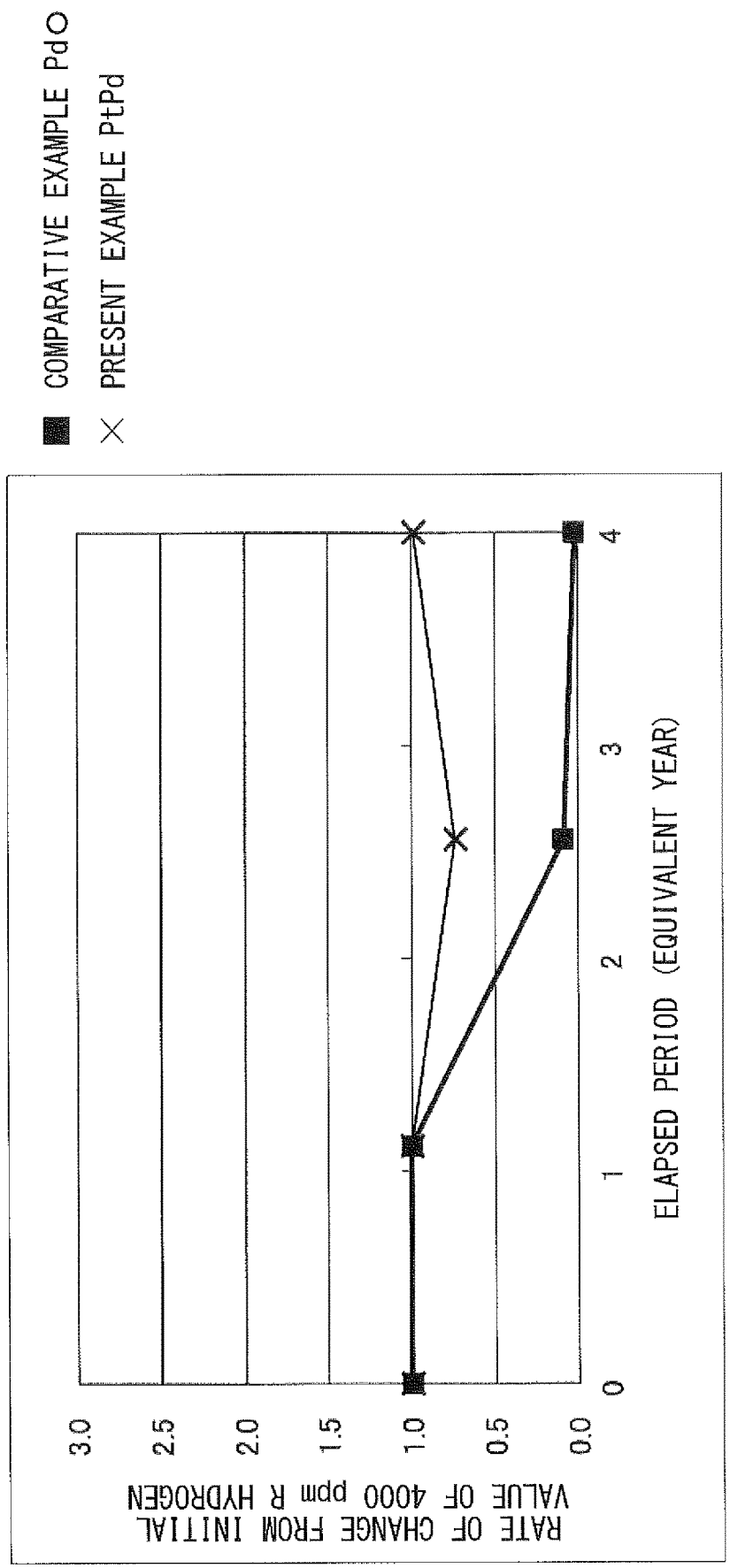
FIG. 13 is a characteristic diagram (no. 4) of a gas sensor manufactured according to the embodiment of the present invention.

FIG. 13 is a characteristic diagram (no. 4) of a gas sensor manufactured according to the embodiment of the present invention. FIG. 13 illustrates a result of examining whether the manufactured gas sensor conforms to the detection of hydrogen.

Namely, in FIG. 13, by using the gas sensor manufactured in the present example and the gas sensor manufactured in the comparative example, a change in a sensor resistance value with respect to 4000 ppm hydrogen gas is measured at an equivalent driving year in an actual using environment, namely, in a case in which the gas sensors above are energized under the high-temperature and high-humidity environment in a cycle of 22.5 seconds. A heater temperature in this case is 300° C. to 400° C.

In this case, the gas detection signal processing unit 15 illustrated in FIG. 9 is set to detect hydrogen $H_2$.

FIG. 13 illustrates that there is no large difference in a range of change during a period to equivalent elapsed year 1.5 between the comparative example and the example of the present invention. However, in the sensor in the comparative example, the sensor resistance value decreases up to 0.1 times as large as an initial resistance value at equivalent elapsed year 2.5, and further decreases at years that follow.

On the other hand, in the sensor in the example of the present invention, the sensor resistance value decreases 0.75 times as large as the initial resistance value at equivalent elapsed year 2.5. However, the sensor resistance value continues to increase almost up to the initial resistance value during a period to equivalent elapsed year 4.

Japanese Laid-Open Patent Publication No. 2007-320847 describes a core-shell ceramic particulate and a method for manufacturing the core-shell ceramic particulate. However, the core-shell ceramic particulate has a core-shell structure in which a core portion is formed of a single type of atom, and therefore there is a problem wherein oxidation activity is low.

In addition, Japanese Patent No. 3624928 discloses a method for manufacturing a platinum/palladium catalyst having a high oxidation activity. However, a supporting method is specified to be manufacture by impregnation with a solution of platinum chloride and palladium chloride, and therefore there is a problem wherein specific processing is required to synthesize a catalyst.

Further, in a catalyst having a conventional core-shell structure described in Japanese Patent No. 4958088, a shell portion is formed by a layer of organic polymer substance. Heat treatment needs to be performed on a core-shell type cerium oxide polymer hybrid particulate so as to generate a cerium oxide porous thin film. Therefore, there is a problem wherein specific processing is required to synthesize a catalyst.

On the other hand, according to an embodiment of the present invention, a core-shell type catalyst with a high oxidation activity in which a core portion is composed of a single metal material and a shell portion is formed so as to have a solid-phase structure composed of two types of metal and oxygen, and a gas sensor including the catalyst, can be provided.

In addition, according to an embodiment of the present invention, a shell portion is formed so as to have a solid-phase structure composed of two types of metal atoms and oxygen, the solid solution structure being expressed by a general formula, $A_{1-x}B_xO_Y$ (where X is a composition that configures A and B, and Y is a composition of oxygen (O)).

Therefore, a higher oxidation activity to hydrogen can be provided, and the core-shell type catalyst cannot be applied only to a catalyst for a gas sensor, but can also be applied to another oxidation catalyst.

Further, various changes can be made to the structure of a catalyst by considering compositions of the solid-phase structure above.

In addition, according to an embodiment of the present invention, supporting can be performed by using a nitrogen aqueous solution as an aqueous solution at the time of supporting, and therefore post-treatment on a powdered catalyst can be reduced.

Further, by employing a gas sensor including a core-shell type catalyst according to an embodiment of the present invention, a first flammable gas (for example, LP gas) and a second flammable gas (for example, methane gas) can be detected, and odorless gas (for example, CO gas) can also be detected by making the heating temperature of a heater layer variable under a high-humidity environment.

The core-shell type catalyst according to the embodiment of the present invention has a higher oxidation activity than that of a conventional catalyst including a single-phase (single-metal-phase) shell layer. Therefore, the core-shell type catalyst is advantageous as a catalyst for a gas sensor that detects CO gas, LP gas, or methane gas, and the core-shell type catalyst can also be used as an oxidation catalyst.

What is claimed is:

1. A core-shell catalyst, consisting of:
a catalyst particulate consisting of
a core portion consisting of a metal material consisting of a single metal element which is a first metal element, and
a shell portion having a solid-phase structure that is comprised of
a plurality of metal materials including the first metal element and a second metal element that is different from the first metal element and
a non-metal material consisting of a single non-metal element; and
a catalyst support for immobilizing the catalyst particulate.

2. The core-shell catalyst according to claim 1, wherein the first and second metal elements each are selected from among Pt, Pd, Ag, Au, Ni, Sn, Ir, Rh, Ru, Re, and Co.

3. The core-shell catalyst according to claim 1, wherein an atomic ratio of the first metal element and the second metal element is 1:1.

4. The core-shell catalyst according to claim 1, wherein the solid-phase structure of the shell portion is composed of the first metal element and the second metal element, and oxygen which are expressed by the formula:

$$A_{1-X}B_XO_Y,$$

where the first element, the second element, and the oxygen are represented as A, B and O, respectively, wherein X is a positive number smaller than 1, and Y is a number greater than 0.

5. The core-shell catalyst according to claim 4, wherein the first and second metal elements are Pd and Pt, respectively, X being equal to 0.5, Y being equal to or less than 1.

6. The core-shell catalyst according to claim 1, wherein the catalyst support includes a metal oxide which is one of $Al_2O_3$, $ZrO_2$, $Cr_2O_3$, $Fe_2O_3$, $Ni_2O_3$, or $SiO_2$.

7. The core-shell catalyst according to claim 1, wherein the solid-phase structure of the shell portion is a solid-solution structure comprised of the plurality of metal materials and the non-metal material.

8. A gas sensor, comprising a gas detection unit for detecting a target gas, the gas detection unit including an absorption layer, the absorption layer including core-shell catalysts according to claim 1.

9. A gas sensor, comprising:
a gas detection unit configured to detect whether a target gas exists, the gas detection unit including
an absorption layer that absorbs the target gas to be detected and includes core-shell catalysts according to claim 1,
a gas sensing layer that senses the target gas, and
a heater layer that heats the gas sensing layer; and
a heater layer drive unit configured to heat the heater layer to be within the range 80° C. to 250° C.

10. A gas sensor, comprising:
a gas detection unit configured to detect whether a target gas exists, the gas detection unit including
an absorption layer that absorbs the target gas to be detected and includes core-shell catalysts according to claim 1,
a gas sensing layer that senses the target gas, and
a heater layer that heats the gas sensing layer; and
a heater layer drive unit configured to heat the heater layer to be within the range 300° C. to 400° C.

11. A gas sensor, comprising:
a gas detection unit configured to detect whether a target gas exists, the gas detection unit including
an absorption layer that absorbs the target gas to be detected and includes core-shell catalysts according to claim 1,
a gas sensing layer that senses the target gas, and
a heater layer that heats the gas sensing layer; and
a heater layer drive unit configured to heat the heater layer to be within the range 350° C. to 450° C.

12. The gas sensor according to claim 9, wherein
the heater layer is heated to be within the range 80° C. to 250° C. by intermittently driving the heater layer drive unit, and
the gas sensing layer senses a CO gas as the target gas thought the gas absorption layer.

13. The gas sensor according to claim 10, wherein
the heater layer is heated to within the range 300° C. to 400° C. by intermittently driving the heater layer drive unit, and
the gas sensing layer senses a liquefied petroleum gas as the target gas thought the gas absorption layer.

14. The gas sensor according to claim 11, wherein
the heater layer is heated to within the range 350° C. to 450° C. by intermittently driving the heater layer drive unit, and
the gas sensing layer senses a methane gas as the target gas thought the gas absorption layer.

15. The gas sensor according to claim 12, further comprising a detection signal processor, wherein
the gas detection unit outputs a gas detection signal including a change between an initial resistance value and a current resistance value that are sensed by the gas sensing layer, and
the detection signal processor detects the target gas from the gas detection signal.

16. The gas sensor according to claim 13, further comprising a detection signal processor, wherein the gas detection unit outputs a gas detection signal including a change between an initial resistance value and a current resistance value that are sensed by the gas sensing layer, and the detection signal processor detects the target gas from the gas detection signal.

17. The gas sensor according to claim 14, further comprising a detection signal processor, wherein the gas detection unit outputs a gas detection signal including a change between an initial resistance value and a current resistance value that are sensed by the gas sensing layer, and the detection signal processor detects the target gas from the gas detection signal.

* * * * *